(12) United States Patent
Gharibadeh

(10) Patent No.: US 6,572,643 B1
(45) Date of Patent: Jun. 3, 2003

(54) ENDOPROSTHESIS DELIVERY CATHETER ASSEMBLY AND METHOD

(75) Inventor: Ramsin Gharibadeh, San Jose, CA (US)

(73) Assignee: Vascular Architects, Inc., San Jose, CA (US)

(*) Notice: Subject to any disclaimer, the term of this patent is extended or adjusted under 35 U.S.C. 154(b) by 196 days.

(21) Appl. No.: 09/618,974

(22) Filed: Jul. 19, 2000

(51) Int. Cl.[7] .................................................. A61F 2/06
(52) U.S. Cl. ....................... 623/1.11; 623/1.22; 606/108
(58) Field of Search ............................... 623/1.11, 1.12, 623/1.22; 606/108, 194, 198

(56) References Cited

U.S. PATENT DOCUMENTS

| | | |
|---|---|---|
| 4,665,918 A | 5/1987 | Garza et al. |
| 5,201,757 A | 4/1993 | Heyn et al. |
| 5,476,505 A | 12/1995 | Limon |
| 5,545,200 A | 8/1996 | West et al. |
| 5,776,142 A | 7/1998 | Gunderson |
| 6,027,516 A | 2/2000 | Kolobow et al. |
| 6,238,430 B1 * | 5/2001 | Klumb et al. .............. 623/1.11 |

* cited by examiner

Primary Examiner—Julian W. Woo
(74) Attorney, Agent, or Firm—James F. Hann; Haynes Beffel & Walfeld LLP

(57) ABSTRACT

An endoprosthesis delivery catheter assembly comprises a placement catheter having first and second catheter shafts. A handle includes a body and an actuator mounted to the body for movement relative to the body. The proximal portions of the first and second catheter shafts are mounted to the handle. At least one of the proximal portions of the first and second catheter shafts are drivenly coupled to the actuator so that movement of the actuator causes rotary and/or axial movement of the first and second catheter shafts relative to one another. The actuator may be mounted to the body for both rotary and axial movement relative to the body so that rotary and axial movement of the actuator causes corresponding relative rotary and axial movement of the first and second catheter shafts. The number of turns and/or the length of the coiled endoprosthesis may be selectively changed using a single actuator and then released from the catheter.

30 Claims, 7 Drawing Sheets

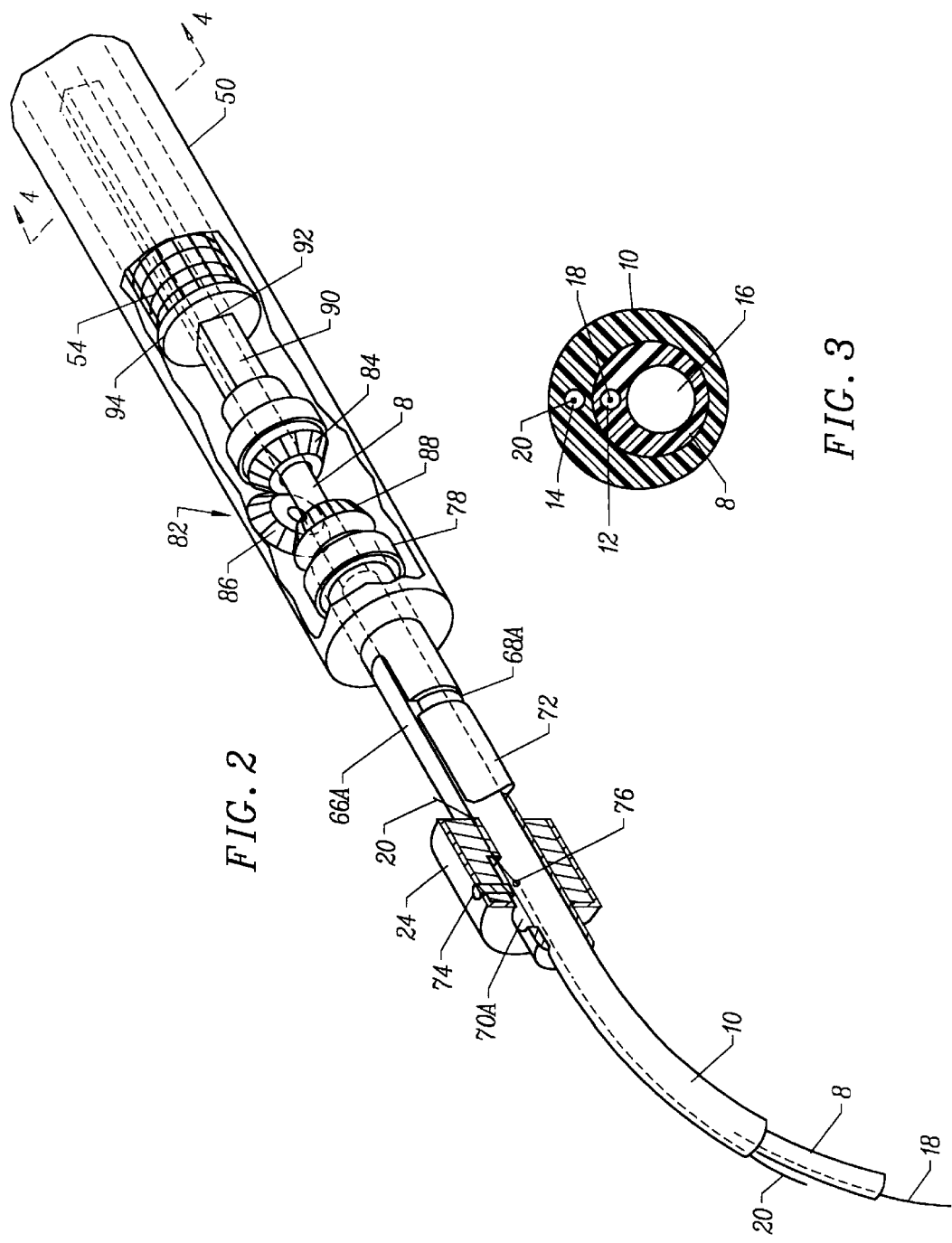

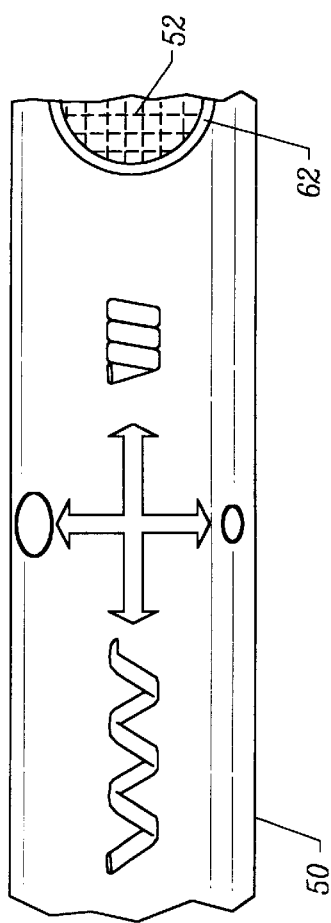
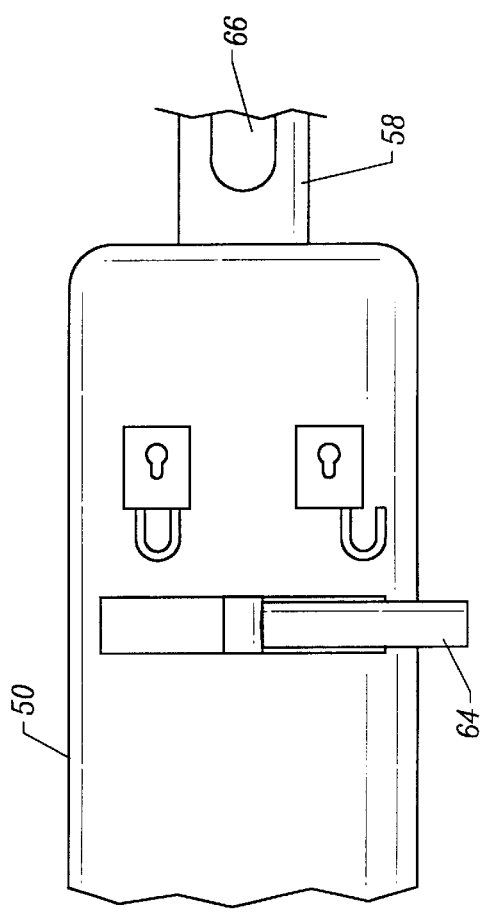
FIG. 9A
FIG. 9B

ENDOPROSTHESIS DELIVERY CATHETER ASSEMBLY AND METHOD

CROSS-REFERENCES TO RELATED APPLICATIONS

This is related to the following: U.S. patent application Ser. No. 09/258,542 filed Feb. 26, 1999, U.S. patent application Ser. No. 09/400,952 filed Sep. 22, 1999 and U.S. patent application Ser. No. 09/400,955 filed Sep. 22, 1999.

STATEMENT AS TO RIGHTS TO INVENTIONS MADE UNDER FEDERALLY SPONSORED RESEARCH AND DEVELOPMENT

None

BACKGROUND OF THE INVENTION

The present invention relates to the endoluminal placement of prostheses, particularly within the vascular system for the treatment of cardiovascular disease, such as vascular stenoses, dissections and other tissue separation conditions, aneurysms, and the like. The apparatus and methods, however, are also useful for placement in other body lumens, such as the ureter, urethra, biliary tract, esophageal, bronchial, gastrointestinal tract and the like, for the treatment of other conditions which may benefit from the introduction of a reinforcing or protective structure within the body lumen. The prostheses will be placed endoluminally. As used herein, "endoluminally" will mean placement by percutaneous or cutdown procedures, wherein the prosthesis is transluminally advanced through the body lumen from a remote location to a target site in the lumen. In vascular procedures, the prostheses will typically be introduced "endovascularly" using a catheter over a guidewire under fluoroscopic guidance. The catheters and guidewires may be introduced through conventional access sites to the vascular system, such as through the femoral artery, or brachial and subclavian arteries, for access to the target site.

An endoluminal prosthesis typically comprises at least one radially expansible, usually cylindrical, body segment. By "radially expansible," it is meant that the body segment can be converted from a small diameter configuration (used for endoluminal placement) to a radially expanded, usually cylindrical, configuration which is achieved when the prosthesis is implanted at the desired target site. The prosthesis may be non-resilient, e.g., malleable, thus requiring the application of an internal force to expand it at the target site. Typically, the expansive force can be provided by a balloon catheter, such as an angioplasty balloon for vascular procedures. Alternatively, the prosthesis can be self-expanding. Such self-expanding structures may be provided by a temperature-sensitive superelastic material, such as Nitinol, which naturally assumes a radially expanded condition once an appropriate temperature has been reached. The appropriate temperature can be, for example, a temperature slightly below normal body temperature; if the appropriate temperature is above normal body temperature, some method of heating the structure must be used. Another type of self-expanding structure uses resilient material, such as a stainless steel or superelastic alloy, forming the body segment so that it possesses its desired, radially-expanded diameter when it is unconstrained, e.g., released from radially constraining forces of a sheath. To remain anchored in the body lumen, the prosthesis will remain partially constrained by the lumen. The self-expanding prosthesis can be delivered in its radially constrained configuration, e.g. by placing the prosthesis within a delivery sheath or tube and retracting the sheath at the target site. Such general aspects of construction and delivery modalities are well-known in the art.

The dimensions of a typical endoluminal prosthesis will depend on its intended use and desired anatomy. Typically, the prosthesis will have a length in the range from 0.5 cm to 5 cm, usually being from about 0.8 cm to 5 cm, for vascular occlusive applications. The small (radially collapsed) diameter of cylindrical prostheses will usually be in the range from about 1 mm to 10 mm, more usually being in the range from 1.5 mm to 6 mm for vascular occlusive applications. The expanded diameter will usually be in the range from about 2 mm to 50 mm, preferably being in the range from about 25 mm to 45 mm for aortic applications.

One type of endoluminal prosthesis includes both a stent component and a graft component. These endoluminal prostheses are often called stent grafts. A stent graft is typically introduced using a catheter with both the stent and graft in contracted, reduced-diameter states. Once at the target site, the stent and graft are expanded. After expansion, the catheter is withdrawn from the vessel leaving the stent graft at the target site.

Grafts are used within the body for various reasons, such as to repair damaged or diseased portions of blood vessels such as may be caused by injury, disease, or an aneurysm. It has been found effective to introduce pores into the walls of the graft to provide ingrowth of tissue onto the walls of the graft. With larger diameter grafts, woven graft material is often used. In small and large diameter vessels, porous fluoropolymers, such as ePTFE, have been found useful.

Coil-type stents can be wound about the catheter shaft in torqued compression for deployment. The coil-type stent can be maintained in this torqued compression condition by securing the ends of the coil-type stent in position on a catheter shaft. The ends are released by, for example, pulling on wires once at the target site. See, for example, U.S. Pat. Nos. 5,372,600 and 5,476,505. Alternatively, the endoluminal prosthesis can be maintained in its reduced-diameter condition by a sleeve; the sleeve can be selectively retracted to release the prosthesis. A third approach is the most common. A balloon is used to expand the prosthesis at the target site. The stent is typically extended past its elastic limit so that it remains in its expanded state after the balloon is deflated and removed. One balloon expandable stent is the Palmaz-Schatz stent available from the Cordis Division of Johnson & Johnson. Stents are also available from Medtronic AVE of Santa Rosa, Calif. and Guidant Corporation of Indianapolis, Indiana.

SUMMARY OF THE INVENTION

The present invention is directed to an endoprosthesis delivery catheter assembly and method, the assembly being relatively simple in construction, easy and efficient to use and designed so that the functions are intuitive.

A first aspect of the invention is directed to an endoprosthesis delivery catheter assembly comprising a placement catheter having first and second catheter shafts. A handle includes a body and an actuator mounted to the body for movement relative to the body. The proximal portions of the first and second catheter shafts are mounted to the body. At least one of the proximal portions of the first and second catheter shafts are drivenly coupled to the actuator so that movement of the actuator causes rotary and/or axial movement of the first and second catheter shafts relative to one another. The actuator may be mounted to the body for both rotary and axial movement relative to the body so that rotary and axial movement of the actuator causes corresponding relative rotary and axial movement of the first and second catheter shafts.

Another aspect of the invention is directed to a method for placing a coiled endoprosthesis at a target site in a patient including locating a coiled endoprosthesis, mounted to a distal portion of a placement catheter, at a target site within a patient. At least one of the number of turns and the length of the coiled endoprosthesis is selectively changed using a single actuator. The coiled endoprosthesis is then released from the placement catheter.

In a preferred embodiment, the actuator has two degrees of freedom of movement corresponding to the two degrees of freedom of movement, that is axial movement and rotary movement, of the catheter shafts relative to one another. However, the actuator could be constructed so that a single motion, for example rotary motion, could be sufficient to cause both the number of turns and the length of the endoprosthesis to change. The relationship between the amount of rotary movement versus axial movement of the catheter shafts may, with this alternative embodiment, be fixed or adjustable. Such a design may help prevent the user from wrapping the endoprosthesis too tightly or too loosely. Such a design would likely be more complicated than that disclosed in the preferred embodiment.

Other features and advantages of the invention will appear from the following description in which the preferred embodiment has been set forth in detail in conjunction with the accompanying drawings.

BRIEF DESCRIPTION OF THE DRAWINGS

FIG. 2 is an enlarged view of a portion of the assembly of FIG. 1 with portions broken away to show the construction details;

FIGS. 3, 4 and 5 are cross sectional views taken along lines 3—3, 4—4 and 5—5 of FIG. 1;

FIGS. 9A and 9B are enlarged views of portions of the handle of FIG. 1 illustrating functional indicia on the handle body adjacent to the access openings and lock, respectively.

DESCRIPTION OF THE SPECIFIC EMBODIMENTS

Figure 1:
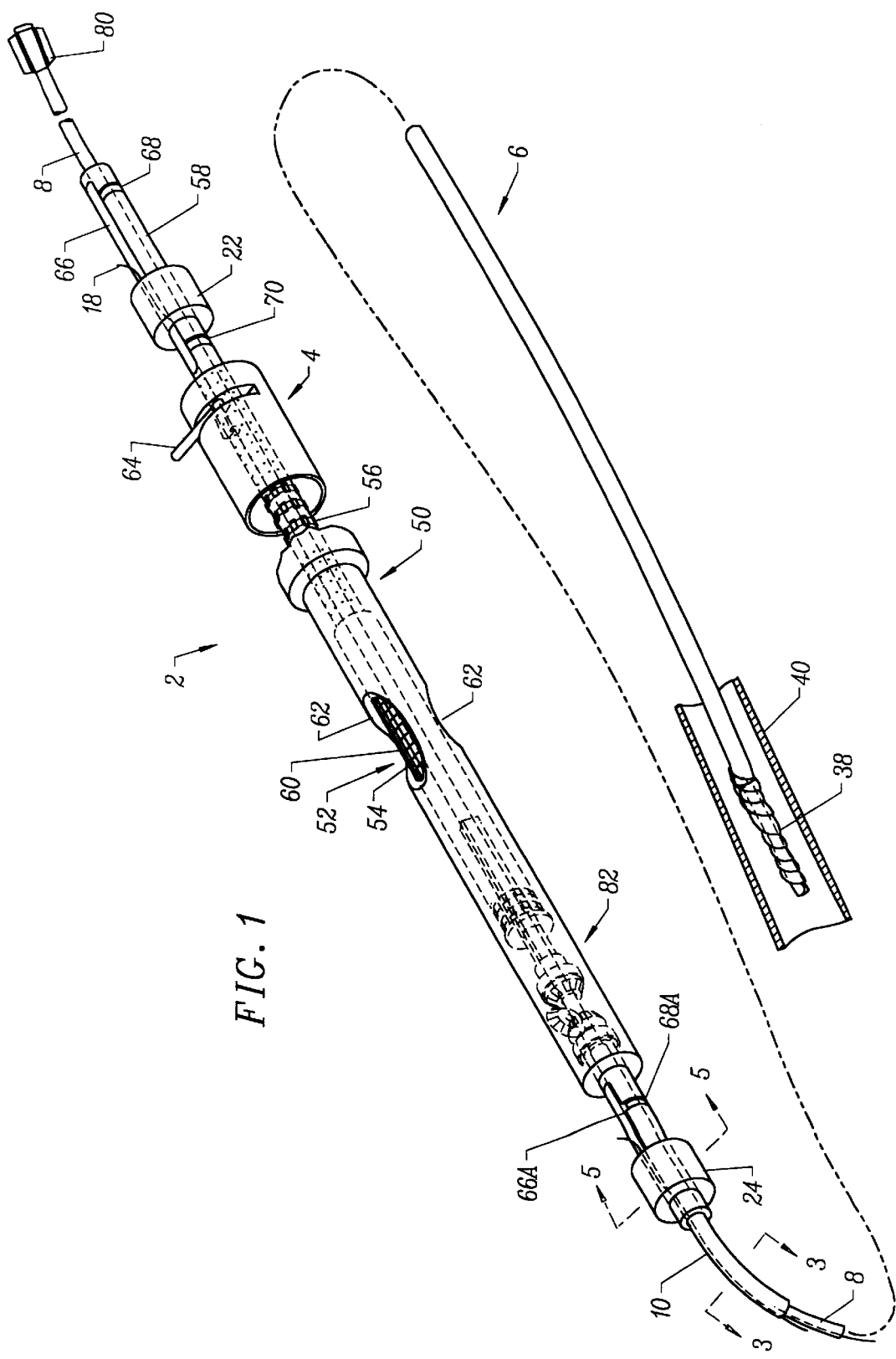
FIG. 1 is an overall view of an endoprosthesis assembly made according to the invention with a helically coiled stent graft, tightly wound about the distal end of the placement catheter, shown within a tubular vessel prior to release.
Figure 5:
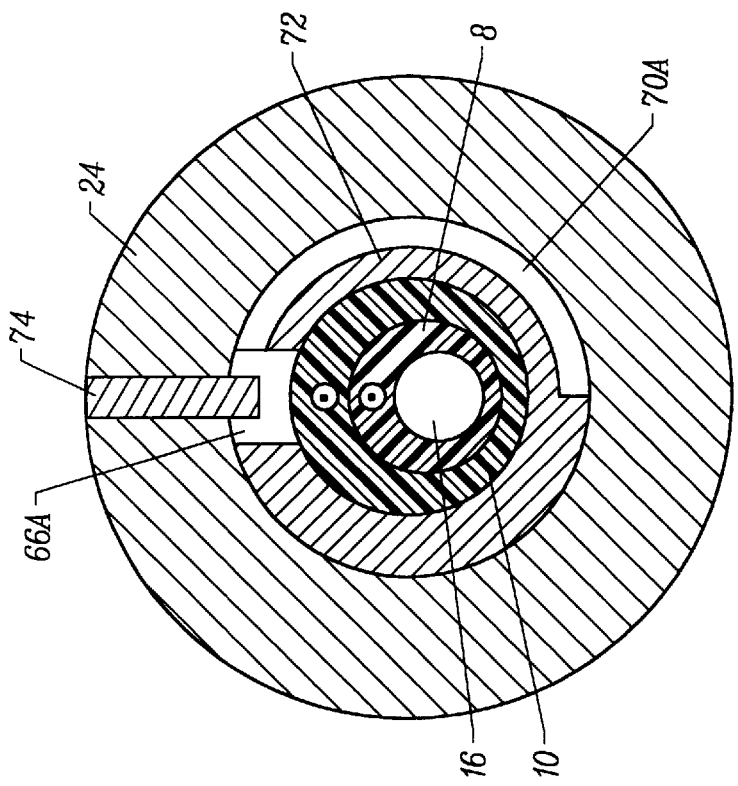
Figure 4:
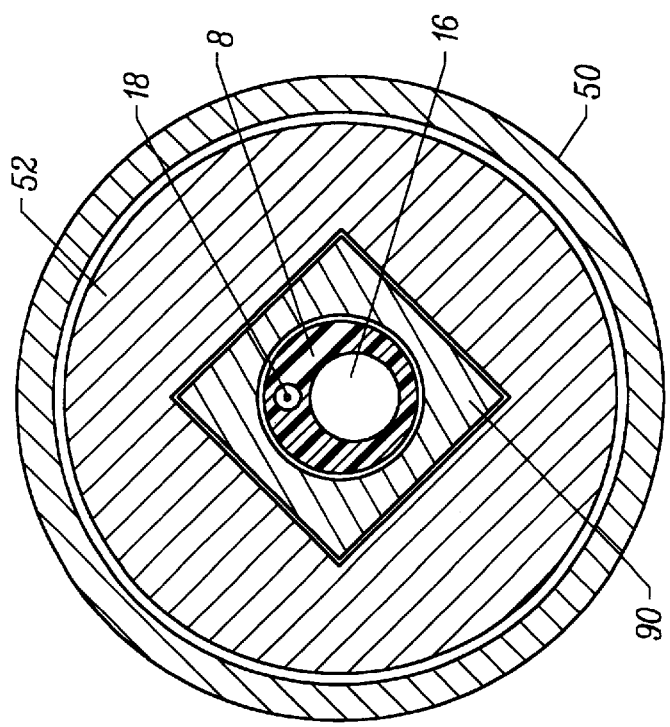
Figure 8:
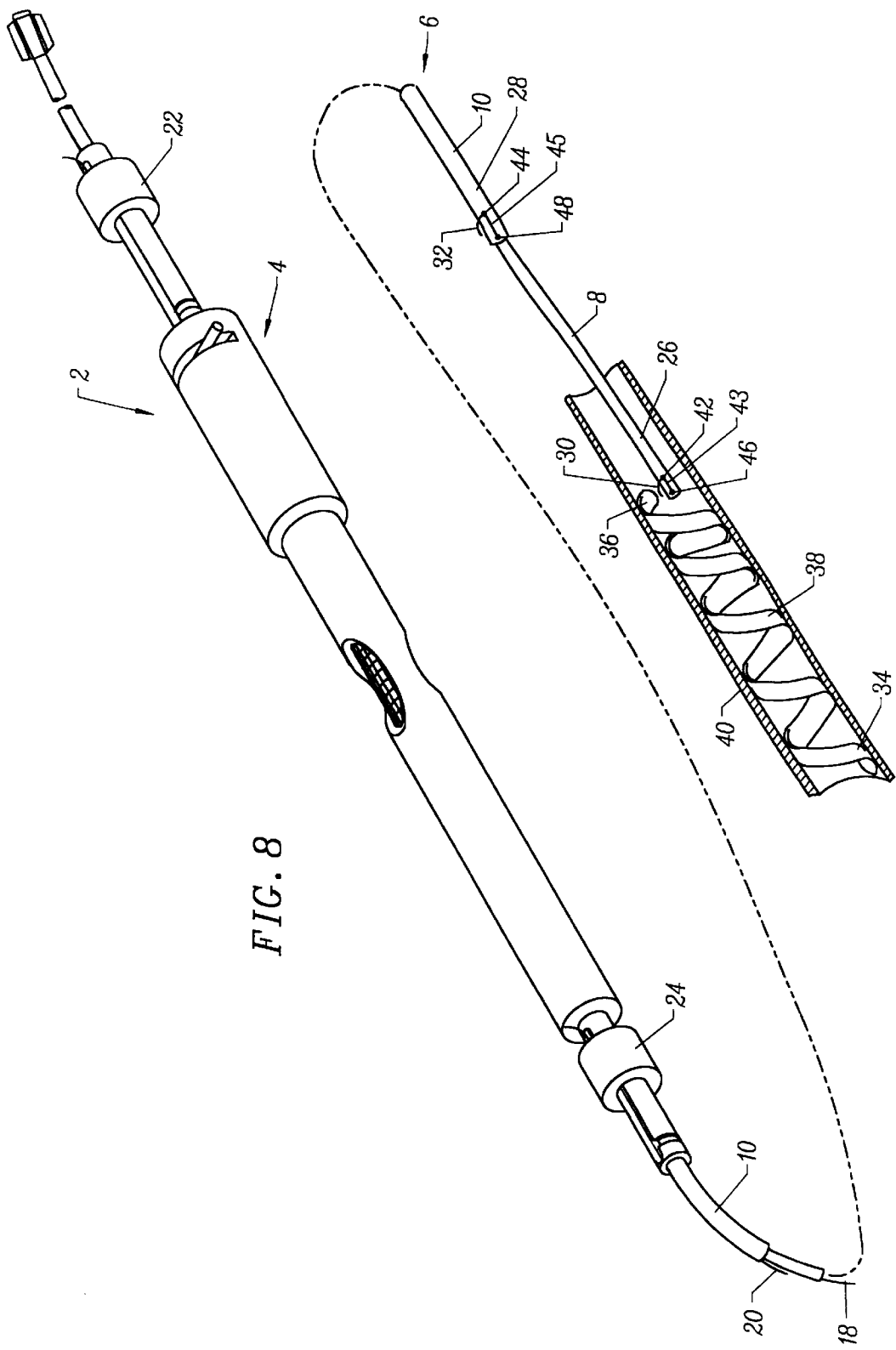
FIG. 8 illustrates the deployed stent graft, the stent graft having been released from the placement catheter by movement of the first and second pull wire actuators.

FIG. 1 is an overall view of an endoprosthesis delivery catheter assembly 2 including a handle 4 and a placement catheter 6 extending from the handle. As seen in more detail in FIGS. 2 and 3, placement catheter 6 includes an outer catheter shaft 10 slidably housing an inner catheter shaft 8. Catheter shafts 8, 10 define respective pull wire lumens 12, 14 while inner catheter shaft 8 defines a main lumen 16 for passage of, for example, a guidewire and/or a flushing liquid. As shown in FIG. 8, inner catheter shaft 8 extends past the distal end of outer catheter shaft 10. First and second pull wires 18, 20 pass through pull wire lumens 12, 14 and have their proximal ends secured to first and second pull wire actuators 22, 24 of handle 4. The distal ends 30, 32 of pull wires 18, 20 extend to the distal ends 26, 28 of catheter shafts 8, 10.

The distal ends 30, 32 of pull wires 18, 20 are used to secure the ends 34, 36 of a coiled stent graft type of endoprosthesis 38 to the distal end of placement catheter 6. As shown in FIG. 1, endoprosthesis 38 is tightly wound about the distal end of placement catheter 6 during placement into a vessel 40. Distal ends 30, 32, see FIG. 8, pass out of lumens 12, 14 through proximal ends 42, 44 of slots 43, 45 formed through shaft 8, pass through the ends 34, 36 of endoprosthesis 38 and then back through distal ends 46, 48 of slots 43, 45 and into lumens 12, 14. Other types of remotely releasing structure can also be used. For example, a single pull wire having a branched end could be used to simultaneously release both distal and proximal ends 34, 36 of endoprosthesis 38; this would, however, eliminate some of the flexibility of placement achievable when the ends are separately releasable.

Figure 6:
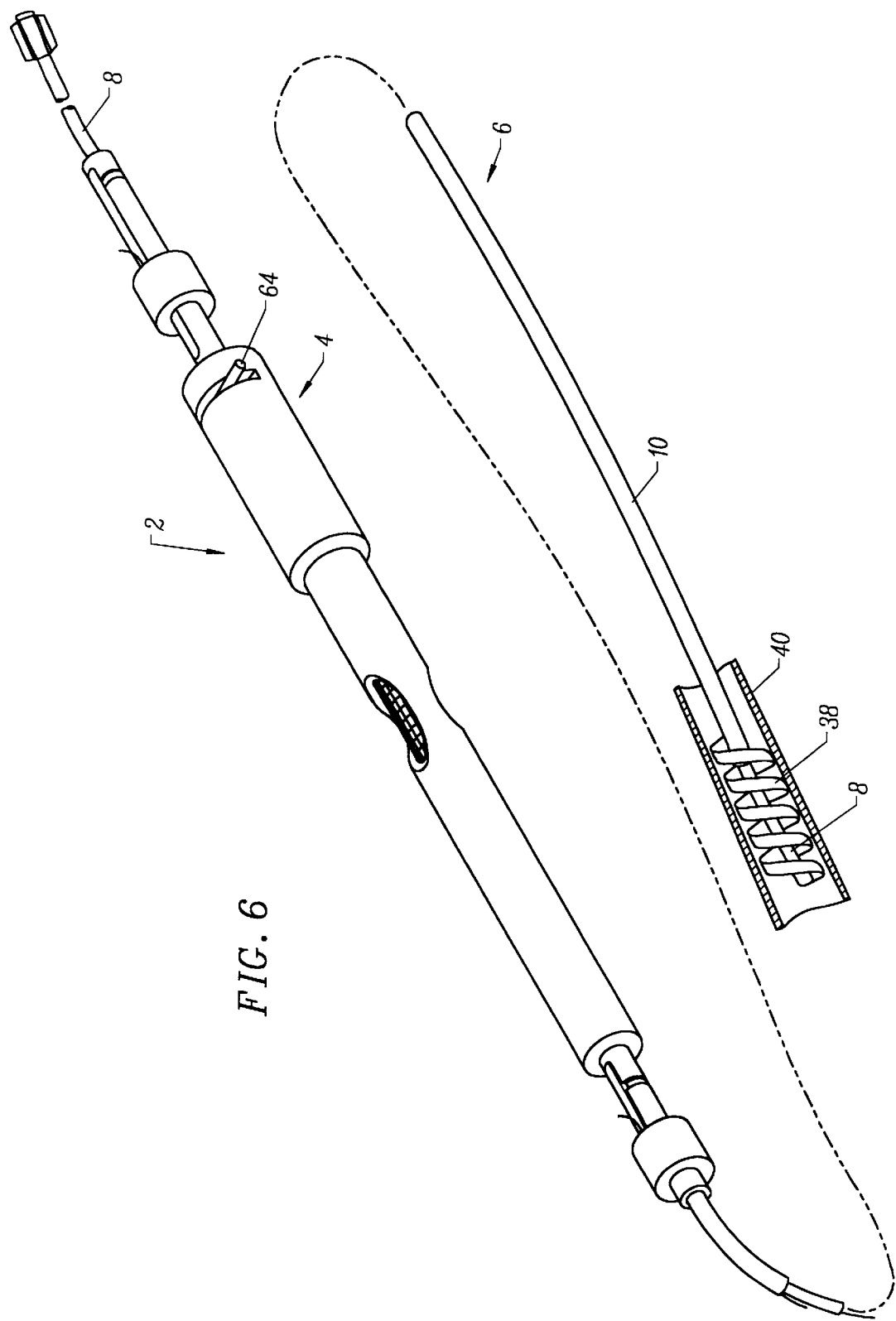
FIG. 6 is a view similar to that of FIG. 1 but showing the stent graft partially uncoiled by rotating the inner and outer catheter shafts in opposite directions.
Figure 7:
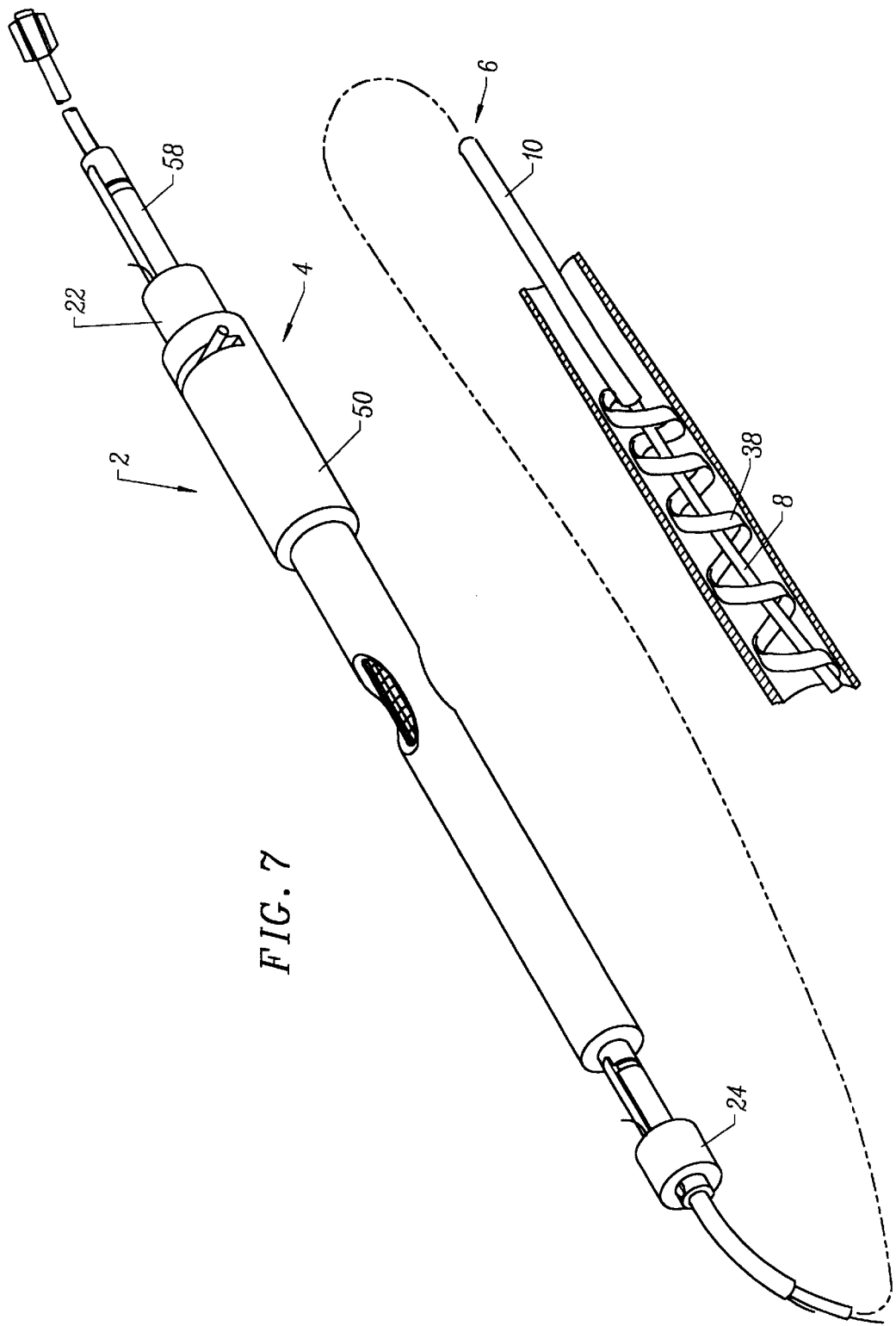
FIG. 7 is a view similar to FIG. 5 but following the longitudinally movement of the actuator shaft causing the inner catheter shaft to slide distally through the outer catheter shaft thus causing the stent graft to increase in length prior to deployment.

Prior to being released at the target site, endoprosthesis 38 may be partially unwound by rotating inner and outer catheter shafts 8, 10 relative to one another; see FIG. 6. In addition, by sliding inner catheter shaft 8 within outer catheter shaft 10 the length of endoprosthesis may be adjusted prior to release; see FIG. 7. This permits the user to at least partially expand endoprosthesis 38 at a target site and determine, typically through remote visualization techniques, whether the placement is proper; if not, endoprosthesis 38 may be returned to a tightly wound configuration, such as shown in FIG. 1, so that it may be repositioned and re-deployed before being released from placement catheter 6.

The relative rotation of inner and outer catheter shafts 8, 10, the actuation of pull wires 18, 20 and the axial and/or longitudinal sliding of inner catheter shaft 8 within outer catheter shaft 10 are all controlled by the user through handle 4. Handle 4 includes a generally cylindrical, hollow body 50 housing an elongate actuator 52. Actuator 52 can slide axially and rotate within body 50. Actuator 52 includes a forward section 54, a middle section 56 and a rear section 58. Forward section 54 has a roughened outer drive surface 60 accessible to the user through a pair of access openings 62. The user can thus simply and easily move actuator 52 axially and/or rotate the actuator through the manual engagement of actuator 52 through access opening 62. Middle section 56 has a diameter which is somewhat smaller than forward section 54 but has an outer surface configured for engagement by a lock 64. Lock 64 is carried by body 50 and is movable from a locked positioned, shown in FIGS. 1 and 9B, to an unlocked position, shown in FIGS. 6–8. When in the locked position, actuator 52 is prevented from moving within body 50 thus preventing any rotary or longitudinal movement of catheter shafts 8, 10 relative to one another.

Rear section 58 extends outwardly past body 50 and is used to carry first pull wire actuator 22. Extension 58 includes an axially extending slot 66 and a pair of circumferentially extending slots 68, 70, slot 70 being covered by actuator 22 in FIG. 1. The construction of actuator 22 and its function and use will be discussed with reference to actuator 24 and its corresponding slots 66A, 68A and 70A, shown in FIG. 2. Slots 66A, 68A, 70A are formed in a rigid sleeve 72 extending from a distal end of body 50. Sleeve 72 is fixed to outer catheter shaft 10 and rotates with the outer catheter shaft. Actuator 24 has a guide pin 74 which rides along slots 66A, 68A 70A. Rotation of guide pin 74 of actuator 24 into slot 70A prevents the inadvertent movement of pin 74 along slot 66A, which would cause actuator 24 to pull second pull wire 20 thus causing the premature release of one end of endoprosthesis 38. As seen in FIG. 2 wire 10 passes from lumen 14 through an opening 76 in catheter shaft 10, where it is attached to actuator 24, such as with an adhesive or other suitable means.

It is preferred that when pin 74 is aligned with slot 66A, a visual or tactile indication of this alignment is provided. One way is to provide an opening within actuator 24 which is aligned with operational indicia applied to the outside surface of sleeve 72. For example, when pull wire actuator 24 is in a locked or secure position within either of slots 68A or 70A, the window in actuator 24 may expose red indicator indicating a safe (stop) condition. When pin 74 is aligned with slot 66A, the indicator beneath the window in hold down actuator 24 could be a green dot indicating that pull wire actuator may be freely moved along slot 66A (go). Pulling actuators 22, 24 proximally with pins 74 sliding along slots 66, 66A, causes distal ends 30, 32 of pull wires 18, 20 to be pulled out of ends 34, 36, thus releasing ends 34, 36 of endoprosthesis 38. See FIG. 8.

FIG. 2 shows the passage of sleeve 72 into body 50, the proximal end of sleeve 72 being supported by a bearing 78. Outer catheter shaft 10 terminates before bearing 78 while inner catheter shaft 8 continues on through the entire handle 4 and extends out pass actuator shaft extension 58 where it terminates in a flushing port 80.

Sleeve 72 and outer catheter shaft 10 therewith are rotated by a reversing gear train 82. Reversing gear train 82 includes a driving gear 84, an idler gear 86 and a driven gear 88. Driven gear 88 is mounted to the proximal end of sleeve 74 so that rotation of driven gear 88 causes sleeve 72 and outer catheter shaft 10 therewith to rotate relative to body 50 of handle 4. Driving gear 88 is mounted to the end of a square drive shaft 90 which slidably passes through a complementarily shaped opening 92 at the distal end 94 of the forward section 54 of actuator 52. Thus, rotation of actuator 52 in one rotary direction causes outer catheter shaft to rotate in an opposite rotary direction due to the presence of reversing drive train 82. However, axial movement of actuator 52 does not cause any axially movement of outer catheter shaft 10 because shaft 90 slides within actuator 52.

Inner catheter shaft 8 passes through actuator 52 and is secured to actuator 52. Inner catheter shaft 8 thus rotates with and moves axially with actuator 52.

It should be noted that pull wire actuators 22, 24 rotate with their associated pull wires 18, 20 and catheter shafts 8, 10. In addition, pull wire actuator 22 moves axially with inner catheter shaft 8 so that manipulation of actuator 52 does not cause the inadvertent movement of pull wires 18, 20 within their associated lumens 12, 14.

In use, an assembly, such as assembly 2 shown in FIG. 1, is selected and the tightly coiled endoprosthesis 38 is introduced to a target site, typically percutaneously. Once at the target site, lock 64 is moved from its locked position (FIGS. 1 and 9B) to its unlocked position (FIGS. 6–8) which permits the user to rotate and/or axially slide actuator 52 by the direct manipulation of the actuator through openings 62. This permits endoprosthesis 38 to be unwound (see FIG. 6) and/or have its axially length changed (see FIG. 7) prior to being released from placement catheter 6. Once it is determined that endoprosthesis 38 is properly positioned and arranged, pull wire actuators 22, 24 are rotated from their safe positions and pulled axially in a proximal direction thus releasing the endoprosthesis. Pull wire actuators 22, 24 are then rotated so that pins 74 enter slots 68, 68A so to prevent the inadvertent extension of pull wires 18, 20. Placement catheter 6 may then be withdrawn from the patient.

Assembly 2 could be provided to the user with an endoprosthesis mounted to catheter 6. This would facilitate constructing assembly 2 with appropriate stops to prevent endoprosthesis 38 from being wrapped too tightly onto catheter 6, or being axially stretched too much, or being axially contracted too much. Visual indication of excessive manipulation of endoprosthesis 38 could be provided; for example, visual marking could be placed on the outer surface of actuator 52 and one or more windows in body 50 could be provided which would overlie the visual marking when excessive manipulation of endoprosthesis is about to occur.

Other modification and variation can be made to the disclosed embodiment without departing from the subject of the invention as defined in the following claims. For example, other types of reversing drive trains, such as rack and pinion drive trains, could also be used. While it is possible to maintain outer catheter shaft 10 fixed both axially and rotationally relative to handle 4, it is considered to be desirable to have both ends of endoprosthesis 38 rotated in opposite directions rather than having one stationary and the other rotating; also, rotating both catheter shafts 8, 10 in opposite rotary directions permits a relatively simple rotary drive to be used while providing a two-to-one rotary drive output advantage. Also, inner catheter shaft 8 has been shown to extend completely through handle 4; if desired inner shaft 8 could terminate within actuator 52 and a separate flushing tube could be mounted to the proximal end of actuator shaft extension 58; a rotary, fluid-sealing coupling may be used to connect the flushing tube to handle 4. Indicia other than those shown in FIGS. 9A and 9B could be used to indicate the results of movement of actuator 52 and the position of lock 64.

Any and all patents, patent applications and printed publication referred to above are incorporated by reference.

What is claimed is:

1. An endoprosthesis delivery catheter assembly comprising:
   a placement catheter comprising first and second catheter shafts, said catheter shafts each having proximal and distal portions, said catheter shafts lying generally parallel to and adjacent to one another;
   a handle comprising:
      a body; and
      an actuator mounted to the body for movement relative to the body;
   the proximal portions of the first and second catheter shafts being mounted to the handle; and
   the proximal portions of the first and second catheter shafts being drivenly coupled to the actuator so that:
      rotational movement of the actuator relative to the body causes only rotary movement of the first and second catheter shafts relative to one another; and
      axial movement of the actuator relative to the body causes only axial movement of the first and second catheter shafts relative to one another.

2. The assembly according to claim 1 wherein rotational movement of the actuator causes rotary movement of each of the first and second catheter shafts relative to the body and in opposite rotary directions.

3. The assembly according to claim 1 wherein the second catheter shaft is a hollow catheter shaft and houses the first catheter shaft therein so the first catheter shaft may rotate and move axially within the second catheter shaft.

4. The assembly according to claim 1 wherein the first catheter shaft defines a lumen couplable to a fluid flushing port.

5. The assembly according to claim 1 wherein the body is a hollow body.

6. The assembly according to claim 5 wherein the actuator is mounted within the hollow body.

7. The assembly according to claim 6 wherein the actuator comprises a generally cylindrical, tubular actuat or shaft having an outer circumferential drive surface.

8. The assembly according to claim 7 wherein said body has an access opening to provide user access to the drive surface.

9. The assembly according to claim 7 wherein the proximal portion of the first catheter shaft extends completely through the tubular actuator.

10. The assembly according to claim 1 where in the actuator rotatably drives the first catheter shaft, and the proximal portions of the first and second catheter shafts are rotatably mounted to the body.

11. The assembly according to claim 10 wherein the actuator further comprises an actuator shaft and a reversing rotary drive train operably coupling the actuator shaft and the proximal portion of the second catheter shaft so that rotation of the actuator causes the first and second catheter shafts to rotate in opposite directions relative to each other and to the body.

12. The assembly according to claim 11 wherein the reversing drive train comprises a reversing gear train.

13. The assembly according to claim 10 wherein the proximal portion of the second catheter shaft is mounted to the body at a fixed axial position relative to the body.

14. The assembly according to claim 1 further comprising an endoprosthesis release assembly extending along the catheter configured to permit user to release an endoprosthesis from a distal end of the catheter.

15. The assembly according to claim 14 wherein t he endoprosthesis release assembly comprises:
   first and second endoprosthesis hold-down actuators movably mounted to respective ones of the first and second catheter shafts; and
   first and second endoprosthesis hold-downs carried by respective ones of the first and second catheter shafts and extending from respective ones of the first and second stent hold-down actuators.

16. The assembly according to claim 15 wherein the first and second endoprosthesis hold-down actuators are movable between endoprosthesis-secured and endoprosthesis-released positions.

17. The assembly according to claim 16 wherein the first and second endoprosthesis hold-down actuators comprises visual indicia indicating the immediate capability of moving said actuators between said endoprosthesis-secured and endoprosthesis-released positions.

18. The assembly according to claim 1 wherein the handle comprises an actuator lock engageable with the actuator and movable by a user between a locked position, which prevents relative movement between the actuator and the handle, and an unlocked position, which permits relative movement between the actuator and the handle.

19. An endoprosthesis delivery catheter assembly comprising:
   a placement catheter comprising first and second catheter shafts, said catheter shafts each having proximal and distal portions, the second catheter shaft being a hollow catheter shaft housing the first catheter shaft therein;
   a handle comprising:
      a hollow body; and
      a tubular actuator, having an outer circumferential drive surface, mounted within the body for both rotary and axial movement relative to the body;
   the body having an access opening to provide user access to the drive surface;
   the proximal portions of the first and second catheter shafts being rotatably mounted to the body;
   the proximal portion of the first catheter shaft being drivenly coupled to the actuator so that rotary and axial movement of the actuator causes corresponding rotary and axial movement of the first catheter shaft;
   the handle further comprising a reversing drive train operably coupling the actuator and the proximal portion of the second catheter shaft so that rotation of the actuator causes the second catheter shaft to rotate relative to the body and in a direction opposite to the direction of rotation of first catheter shaft;
   the proximal portion of the second catheter shaft being mounted to the body at a fixed axial position; and
   an endoprosthesis release assembly extending along the catheter configured to permit user to release an endoprosthesis from a distal end of the catheter.

20. The assembly according to claim 19 wherein the endoprosthesis release assembly comprises:
   first and second endoprosthesis hold-down wire actuators movably mounted to respective ones of the first and second catheter shafts; and
   first and second endoprosthesis hold-down wires carried by respective ones of the first and second catheter shafts and extending from respective ones of the first and second stent hold-down wire actuators;
   the first and second endoprosthesis hold-down wire actuators being movable between endoprosthesis-secured and endoprosthesis-released positions.

21. A method for placing a coiled endoprosthesis at a target site within a patient comprising:
   locating a coiled endoprosthesis, mounted to a distal portion of a placement catheter, at a target site within a patient, the coiled endoprosthesis comprising turns and a length, said coiled endoprosthesis initially being in a radially contracted state, the placement catheter extending from a handle;
   selectively changing at least one of the number of turns and the length of the coiled endoprosthesis using a single actuator, the actuator movably mounted to the handle;
   the selectively changing the number of turns step being carried out by rotating each of first and second catheter shafts of the placement catheter in opposite rotary directions relative to one another and to the handle, distal and proximal portions of the coiled endoprosthesis being connected to the first and second catheter shafts respectively;
   the selectively changing the length step being carried out by axially sliding the first catheter shaft relative to the second catheter shaft and the handle;
   prior to the selectively changing steps, releasing the actuator from a locked state to an unlocked state to permit the actuator to move relative to the handle; and
   releasing the coiled endoprosthesis from the placement catheter by manipulating at least one wire thereby releasing proximal and distal ends of the endoprosthesis from the placement catheter, the releasing step being carried out by:
changing a release element from a safe state to a release state; and then
moving the release element from an endoprosthesis-engaged position to an endoprosthesis-released position.

22. A method for placing a coiled endoprosthesis at a target site within a patient comprising:
locating a coiled endoprosthesis, mounted to a distal portion of a placement catheter, at a target site within a patient, the coiled endoprosthesis comprising turns and a length, said coiled endoprosthesis initially being in a radially contracted state, the placement catheter extending from a handle;
deciding whether or not to change the number of turns and if yes changing the number of turns of the coiled endoprosthesis using an actuator, the actuator movably mounted to the handle;
deciding whether or not to change the length, and if yes changing the length of the coiled endoprosthesis using the actuator;
the changing the number of turns step comprising rotating first and second catheter shafts of the placement catheter in opposite rotary directions reactive to one another and to the handle, distal and proximal portions of the coiled endoprosthesis being connected to the first and second catheter shafts respectively; and
the changing the length step comprising axially sliding the first catheter shaft relative to the second catheter shaft and the handle.

23. The method according to claim 22 wherein the length changing step is carried out with the second catheter shaft secured to a handle.

24. The method according to claim 22 wherein the number of turns are changed before the length is changed.

25. The method according to claim 22 wherein the releasing step is carried out by manipulating at least one wire.

26. The method according to claim 22 wherein the releasing step is carried out by releasing proximal and distal ends of the endoprosthesis from the placement catheter.

27. The method according to claim 26 wherein the releasing step is carried out by changing a release element from a safe state to a release state and then moving the release element from an endoprosthesis-secured position to an endoprosthesis-released position.

28. The method according to claim 22 wherein the deciding step is carried out with the actuator mounted to the handle, and further comprising releasing the actuator from a locked state to an unlocked state to permit the actuator to move relative to the handle.

29. An endoprosthesis delivery catheter assembly comprising:
a placement catheter comprising first and second catheter shafts, said catheter shafts each having proximal and distal portions, said catheter shafts Lying generally parallel to and adjacent to one another;
a handle comprising:
a body; and
an actuator mounted to the body for movement relative to the body;
the proximal portions of the first and second catheter shafts being rotatably mounted to the handle;
at least one of the proximal portions of the first and second catheter shafts being drivenly coupled to the actuator so that movement of the actuator causes a selected one of rotary movement, axial movement, or both rotary and axial movement of the first and second catheter shafts relative to one another;
the actuator rotatably driving the first catheter shaft; and
the actuator further comprising an actuator shaft and reversing rotary drive train operably coupling the actuator shaft and the proximal portion of the second catheter shaft so that rotation of the actuator causes the first and second catheter shafts to rotate in opposite directions relative to each other and to the body.

30. An endoprosthesis delivery catheter assembly comprising:
a placement catheter comprising first and second catheter shafts, said catheter shafts each having proximal and distal portions, said catheter shafts lying generally parallel to and adjacent to one another;
a handle comprising:
a body;
an actuator mounted to the body for movement relative to the body; and
an actuator lock engageable with the actuator and movable by a user between a locked position, which prevents relative movement between the actuator and the handle, and an unlocked position, which permits relative movement between the actuator and the handle;
the proximal portions of the first and second catheter shafts being mounted to the handle; and
at least one of the proximal portions of the first and second catheter shafts being drivenly coupled to the actuator so that movement of the actuator causes a selected one of rotary movement, axial movement, or both rotary and axial movement of the first and second catheter shafts relative to one another.

* * * * *